United States Patent
Koby et al.

(10) Patent No.: US 7,601,168 B2
(45) Date of Patent: Oct. 13, 2009

(54) EYE PILLOW

(76) Inventors: Aurelia Koby, 4461 Ocean Blvd., San Diego, CA (US) 92109; Ian MacMorran, 886 Cordova St., San Diego, CA (US) 92107

(*) Notice: Subject to any disclaimer, the term of this patent is extended or adjusted under 35 U.S.C. 154(b) by 256 days.

(21) Appl. No.: 11/141,910

(22) Filed: Jun. 1, 2005

(65) Prior Publication Data

US 2006/0036305 A1    Feb. 16, 2006

Related U.S. Application Data (60) Provisional application No. 60/576,204, filed on Jun. 2, 2004.

(51) Int. Cl.
*A61F 7/00* (2006.01)
(52) U.S. Cl. .......... 607/109; 607/112; 607/114
(58) Field of Classification Search ........ 607/96, 607/108–112, 114
See application file for complete search history.

(56) References Cited

U.S. PATENT DOCUMENTS

| | | | | |
|---|---|---|---|---|
| 2,101,628 A | * | 12/1937 | Padelford | 607/109 |
| 2,537,768 A | * | 1/1951 | Laporte | 2/15 |
| 2,796,903 A | | 6/1957 | Gazelle | |
| 3,354,884 A | * | 11/1967 | Rudo | 604/303 |
| 3,552,044 A | * | 1/1971 | Wiele | 36/71 |
| 3,768,485 A | * | 10/1973 | Linick | 607/109 |
| 4,243,041 A | * | 1/1981 | Paul | 607/109 |
| 4,372,318 A | | 2/1983 | Viesturs et al. | |
| 4,513,197 A | * | 4/1985 | Courvoisier et al. | 219/527 |
| 4,850,376 A | * | 7/1989 | DellaVecchia et al. | 128/858 |
| 4,872,217 A | * | 10/1989 | Kitayama | 2/15 |
| 5,119,812 A | | 6/1992 | Angelo | |
| 5,274,865 A | | 1/1994 | Takehashi | |
| 5,344,437 A | | 9/1994 | Pistay | |
| 5,366,491 A | * | 11/1994 | Ingram et al. | 607/108 |
| 5,628,772 A | * | 5/1997 | Russell | 607/109 |
| 5,700,238 A | * | 12/1997 | Hyson | 602/74 |
| 6,241,711 B1 | * | 6/2001 | Weissberg et al. | 604/291 |
| 6,409,746 B1 | * | 6/2002 | Igaki et al. | 607/109 |
| 6,571,799 B1 | * | 6/2003 | Daly | 128/857 |
| 6,623,517 B1 | * | 9/2003 | DeLuisa et al. | 607/109 |
| 6,986,945 B2 | * | 1/2006 | Mushiake et al. | 428/407 |
| 2001/0039442 A1 | * | 11/2001 | Gorge et al. | 607/109 |
| 2003/0056281 A1 | * | 3/2003 | Hasegawa | 2/428 |

OTHER PUBLICATIONS

Printout of http://www.imakproducts.com/product.php?s=16 as downloaded on Jul. 9, 2008, describing "Wrist Cushion for Mouse" product that has been on sale at least as early as Jun. 1, 2003.

* cited by examiner

*Primary Examiner*—Roy D Gibson
*Assistant Examiner*—Kaitlyn E Helling
(74) *Attorney, Agent, or Firm*—Duane Morris LLP

(57) ABSTRACT

A reversible eye pillow provides a set of opposed sides, each formed of a continuous fabric panel that is resiliently stretchable. Each side includes peripheral portions that conform to and contact peripheral portions of a user's eye and a recessed portion that enables a user to open his or her eye with the eye pillow in place. The eye pillow is tightly filled with small bead like thermal storage filling material that maintains a reduced temperature and includes a smooth surface to provide easy deformability of the eye pillow even at reduced temperatures.

19 Claims, 4 Drawing Sheets

EYE PILLOW

RELATED APPLICATION

This application is related to, and claims priority of U.S. provisional application Ser. No. 60/576,204 filed Jun. 2, 2004, the contents of which are hereby incorporated by reference as if set forth in its entirety.

FIELD OF THE INVENTION

The invention is related to orthopedic and ergonomic products that provide support, comfort and relief to a user. In particular, the invention relates to an eye pillow.

BACKGROUND

Persons suffering from migraine and other headaches, sinus pain, tired and puffy eyes and the like, and persons recovering from cosmetic eye surgery and BOTOX® treatments, frequently find it desirable to apply thermal treatment to the affected area, the facial region in the location of the eyes. Thermal treatment such as heat or cold may be employed to reduce swelling, relieve pain, alleviate tension, and provide soothing comfort to the wearer. A traditional practice in applying thermal treatment to a patient has been to employ an ice bag, which may be filled with ice or a combination of ice and water. Ice bags do not conform well to the contours of a user's face and are difficult to hold in place, however. This is due, in part, to the large and defined edges of the ice included in the ice bag. The sharp, pronounced edges of the cubes within the ice bag produce an irregular lumpy surface and make it difficult for the ice bag to have a smooth conformal quality. Moreover, once the ice melts, it must be replenished. Ice must be contained in a waterproof material such as plastic which is uncomfortable when worn against a user's skin.

Various other thermal treatment devices that do not require emptying and replenishing during use or for continued use, have therefore been developed. Included are devices that include one or a plurality of plastic compartments filled with a thermal storage material such as a gelatinous substance. Orthopedic and ergonomic products formed using such a gelatinous substance may become solid when frozen and therefore lose their moldability and their ability to conform to a user's facial anatomy. Moreover, these gelatinous products must also be contained in an impervious material such as plastic which is uncomfortable when worn against a user's skin or requires the use of an additional material component to be comfortable.

It would therefore be desirable to provide an orthopedic/ergonomic device worn by the user in the eye region to produce soothing comfort and which overcomes the shortcomings of prior products. In particular, it would be desirable to provide a product that includes a thermal material filling that need not be replenished, includes a surface comfortable to a user's skin, is moldable at all temperatures including reduced temperatures, and provides soothing coolness, not an icy-cold sensation. It would be further desirable to provide such a device that provides clearance for a user to open his or her eyes while the product is in place and contacting the eye socket area.

SUMMARY OF THE INVENTION

To address these and other needs, and in view of its purposes, the present invention is directed to an eye pillow worn by a user to provide soothing comfort and relief. The eye pillow is formed of a duality of opposed fabric sheets that are joined together. The sheets form opposed sides of the eye pillow, and either side of the reversible eye pillow may be worn against the user's anatomy.

A filling material such as a plurality of beads or pellets is packed between the fabric panels. Each of the opposed sides of the eye pillow is conformable to a user's eye socket anatomy and each side includes recessed portions opposite each of the user's eyes when the eye pillow is positioned on the user. The recessed portions enable the user's eyes to be opened and closed with the eye pillow in contact with the user's eye socket anatomy. The beads may be oval, elliptical or round in shape and may include a dimple. The surfaces of the beads are very smooth, enabling them to slide against each other freely and providing easy deformability of the eye pillow thus enabling it to easily conform to a user's anatomy or any other shape. The fabric faces of the eye pillow provide comfort to the wearer and may be formed of a material that is flaccid or elastically resilient in character. The bead filling is desirably formed of a thermal storage material that retains cold but the beads retain a smooth surface even at reduced temperatures enabling easy deformability, even at reduced temperatures.

BRIEF DESCRIPTION OF THE DRAWING

The present invention is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

DETAILED DESCRIPTION

Figures 1, 1A:
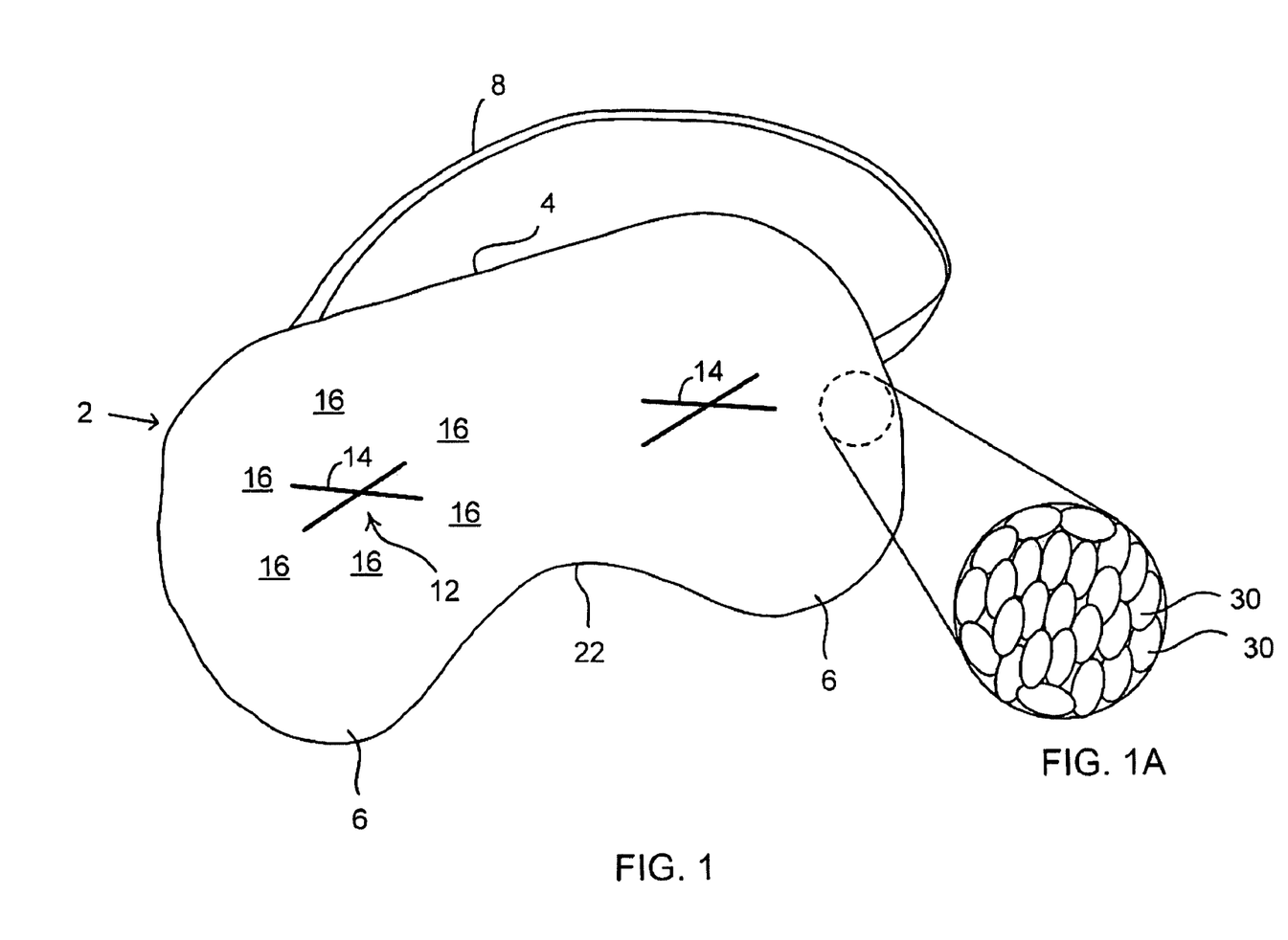
FIG. 1 is a perspective view of an exemplary eye pillow of the invention.
FIG. 1A is a expanded view of the bead filling of an exemplary eye pillow of the invention.

The present invention provides an eye pillow that prevents and treats sinus, migraine and other headaches, soothes tired and puffy eyes, blocks out light and provides cooling relief to the user. The eye pillow may also aid in recovery from cosmetic eye surgery, BOTOX® treatments and the like. The eye pillow covers and peripherally surrounds the eye region when worn by or placed on the user. An exemplary eye pillow embodiment is illustrated in FIG. 1. In other exemplary embodiments, the eye pillow may be larger in size and extend further to cover further peripheral portions of the user's face and head.

The eye pillow is formed of opposed comfortable fabric surfaces (i.e., the "sides") and is filled with a filling material. In one embodiment, the opposed surfaces may be a set of equally sized panels that are peripherally joined such as by stitching or other suitable means. FIG. 1 shows eye pillow 2 which includes a generally level top 4 and a plurality of downwardly extending lobes 6. In other embodiments, the eye pillow may have different shapes. The anatomic shape of eye pillow 2 allows it to conform to the user's face and eyes. The embodiment of FIG. 1 illustrates a continuous single panel 10 that forms one side, i.e., one surface 20, of the eye pillow. It will be shown that a similar panel is formed on the other side of eye pillow 2 and that the panels are peripherally joined. In another embodiment, each surface 20 may be formed of multiple panels, i.e., multiple pieces of fabric joined together. The eye pillow may be reversible and either of the sides of eye pillow 2 may be worn against the user's anatomy. Each side of eye pillow 2 includes recessed portion 12 and peripheral portions 16. When a user wears eye pillow 2, peripheral portions 16 are shaped to conform to and contact the user's eye socket anatomy while recessed portion 12 provides clearance for the user's eye and eyelash when the user opens his or her eyes with the eye pillow in place and contacting the user's anatomy at peripheral portion 16.

Eye pillow 2 includes fastening member 8 which allows the user to wear eye pillow 2. Fastening member 8 secures eye pillow 2 to the wearer's head. An elastic strap or other fastening member may be used. The fastening member may be an elastic strap that extends completely around the wearer's head or it may include straps or an elastic worn behind the wearer's ears to secure eye pillow 2 in place. Fastening member 8 may be fixedly coupled to eye pillow 2 such as by stitching or other conventional means or it may be adjustable with respect to eye pillow 2 or detachably joined to eye pillow 2. In other exemplary embodiments, fastening member 8 may be non-elastic. Straps or strings that tie together, clip together or otherwise fasten together behind the wearer's head, may also be used as fastening member 8. Multiple straps on each of opposed ends of the eye pillow may be used as fastening member 8 in one exemplary embodiment.

Figure 2:
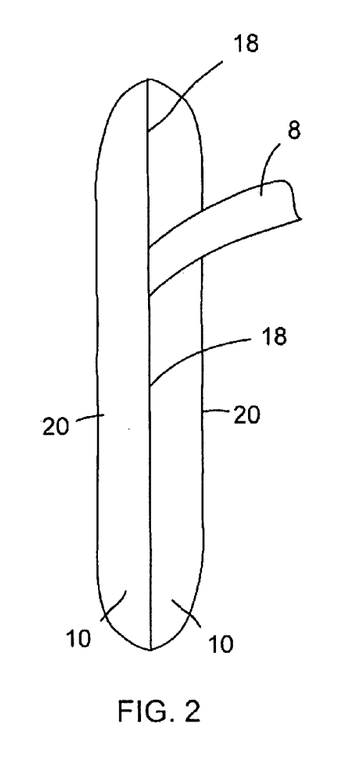
FIG. 2 is a side view of an exemplary eye pillow of the invention.

FIG. 2 is an end view showing opposed surfaces 20 peripherally joined at seam 18 which extends completely around eye pillow 2 to form a closed pouch. Other arrangements may be used in other exemplary embodiments, however. Surfaces 20 are advantageously formed of a comfortable fabric material and may be formed of a continuous single panel, i.e., one piece of fabric, or multiple panels. Each panel may be formed of a fabric that may be flaccid or, resiliently stretchable, and preferably breathable. Various fabrics such as cotton, cotton Lycra, other spandex materials or materials made of other synthetic or natural fibers, may be used. For example, fabrics such as silk or wool or other textiles may be used in other exemplary embodiments. The material may be resilient in orthogonal directions and can provide different degrees of stretching strength. The material and eye pillow 2 may be washable. Fastening member 8 is advantageously joined to eye pillow 2 at seam 18 to accommodate the reversibility of the eye pillow, but other configurations may be used in other exemplary embodiments. In another exemplary embodiment at least part of the peripheral edge of eye pillow 2 is seamless.

Figure 3:
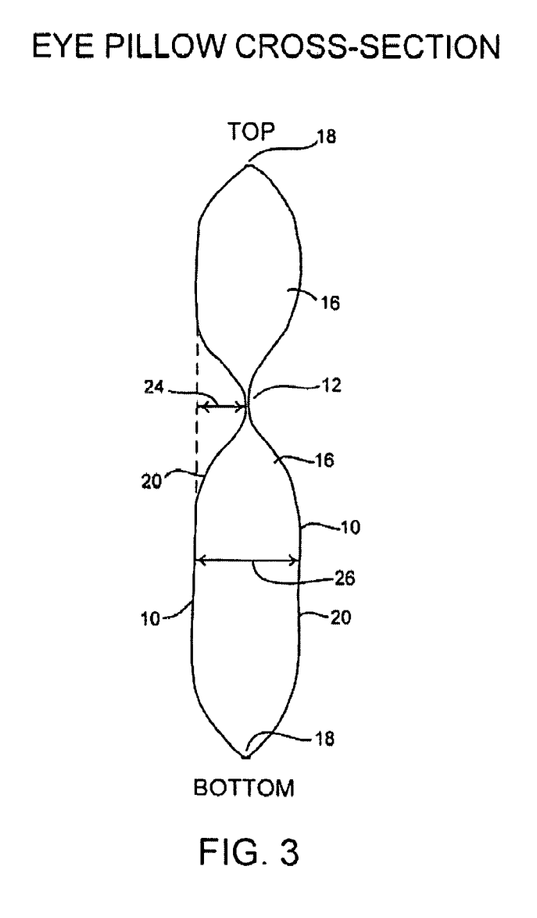
FIG. 3 is a partial cross-sectional view of an exemplary eye pillow of the invention.

FIG. 3 is a partial cross sectional view of the eye pillow illustrating opposed surfaces 20, but the filler material that fills the eye pillow is not shown. Now referring to FIGS. 1 and 3, eye pillow 2 is shaped to conform to the anatomy of the user's face and each of downwardly extending lobes 6, separated by an indentation 22 to accommodate the user's nose, include peripheral portions 16 to contact the user's eye socket area, and recessed portions 12 corresponding to the position of the user's eyeballs. Recessed portions 12 may be formed by joining together opposed surfaces 20. The coupling of the opposed surfaces provides dimples or darts on each side. According to this exemplary embodiment, the thickness of eye pillow 2 is essentially the thickness of the two conterminously joined panels/surfaces at recessed portions 12 as there is no filling material therebetween. Dimpled or recessed portion 12 may laterally extend a distance that is at least the width of an eyeball. The opposed surfaces may be joined by stitching or other suitable means. When stitching is used, an "x" stitch such as shown in FIG. 1, or other stitching configurations, may be used. In other exemplary embodiments, the opposed surfaces may be permanently or detachably joined using other suitable means. Depth 24 may vary and is advantageously chosen to provide clearance within which the use's eyeball and eyelashes may move when peripheral portions 16 contact the user's eye socket anatomy. As such, the wearer may open and move his or her eyes freely with the eye pillow maintaining undisturbed contact with surrounding portions such as the wearer's eyebrows, forehead, cheek, nose and other parts of the wearer's eye socket i.e., at peripheral portion 16, for added comfort. Maximum depth 26 between opposed surfaces 20 of eye pillow 2, may range from 0.25 inch to 2 or 3 inches according to one embodiment.

As shown in FIG. 1A, an expanded cut-away view of an internal portion of eye pillow 2, filling material 30 is disposed between the opposed surfaces of the eye pillow and provides a completely deformable or moldable eye pillow that can be arranged to contact and conform to the contours of the wearer's face. No rigid or other support structure is required to provide a preferred orientation. Filling material 30 may be tightly packed within eye pillow 2 in an exemplary embodiment. Filling material 30 is chosen to provide complete and smooth moldability that enables the eye pillow to conform to various wearers, various locations and various positions. Filling material 30 is advantageously formed of thermal storage material capable of maintaining a reduced temperature for an extended period of time. By reduced temperature, it is meant that the temperature of the thermal storage material is lower than that of the ambient environment. The reduced temperature may be a temperature at or below 32° F., a temperature at or below 40° F., or any temperature that is less than room temperature. The eye pillow may be stored in a household refrigerator or freezer, for example. Filling material 30 provides soothing cool relief without the shock, icy cold feeling of ice or gel. Filling material 30 provides the eye pillow 2 with a comfortable coolness as opposed to a freezing cold sensation. As opposed to ice which has a temperature of 32° F. or lower, filling material 30 may be maintained at reduced temperatures greater than 32° F. Since filling material 30 is formed of a population of small beads with tiny air pockets between the beads, eye pillow 2 provides a more comfortable cool than a freezing cold as the surface that contacts the user is not necessarily a continuous surface with the same temperature at or below 32° F. The smooth conformal nature of eye pillow 2 provided by filling material 30 is more comfortable than the lumpy surface of an ice bag which includes sharp or hard edges that contact particular points on the user's skin and may result in pressure points of extreme cold. The thermal storage material used to form filling material 30 may additionally or alternatively be chosen to retain heat and provide soothing warmth by heating up to a temperature below the melting temperature. Various thermal storage materials may be used.

Figure 4:
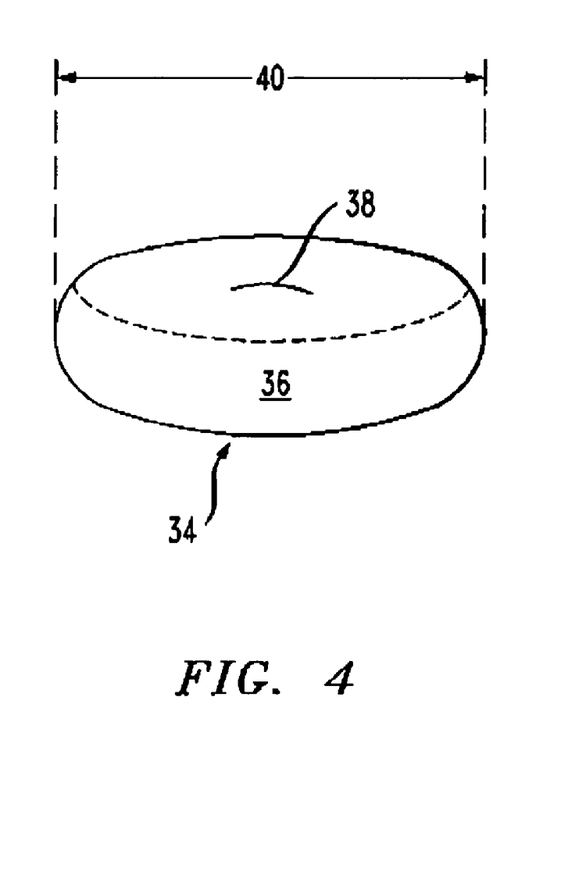
FIG. 4 is perspective view of exemplary beads used in the eye pillow of the present invention.

Filling material 30 may be a granular filling material that is pellet or bead-shaped. The pellets or beads (hereinafter referred to as beads) may be egg-shaped, oval, elliptical, disc shaped or round without sharp edges and with a completely smooth exterior. Filling material 30 may optionally include a lubricating material between and/or coating the beads. An exemplary bead is shown in FIG. 4. Bead 34 includes exterior surface 36 and optionally may include one or more dimples such as dimple 38. In an exemplary embodiment, beads 34 may be formed of low density polyethylene ("LDPE"), and may be natural or semi-clear white in color. They may be injection molded or extrusion type LDPE particles. Beads 34 include no sharp edges and surface 36 is a smooth surface having an average surface roughness of less than 100 nm in one exemplary embodiment enabling the beads 34 that form filling material 30 to slide easily and freely against and past each other. Surface 36 may advantageously be polished to enhance smoothness. A powdery coating may optionally be added to filling material 30, in particular on surfaces 36 of beads 34. The powdery coating may be a mold release agent formed of an amide or other materials, and which acts as a lubricant that promotes smooth sliding of the beads.

Exemplary illustrated disc shaped bead 34 includes a pair of opposed round or oval surfaces. Length 40 may be chosen to be less than or equal to 4.5 millimeters in one exemplary embodiment. Beads 34 may include dimensions of 3 millimeters×4.5 millimeters×2 millimeters and a density of 0.910 to 0.935 grams per cubic centimeter but other sizes and densities may be used in other exemplary embodiments, however. In another exemplary embodiment, beads 34 may include dimensions of about 6 millimeters×4 millimeters×3 millimeters. The exemplary dimensions provided are illustrative but not restrictive of the bead dimensions as other dimensions may be used in other exemplary embodiments. The beads may include at least one dimple. Filler material 30 is packed tightly enough within eye pillow 2 so that eye pillow is deformable or moldable as the beads redistribute responsive to contact surfaces and positioning by the wearer. When eye pillow 2 is in contact with a user, a gentle massaging action is created by filling material 30 when pressure such as a gentle rolling action is applied to eye pillow 2. The materials of surfaces 20 or panels 10 may be chosen in conjunction with the packing density such that eye pillow 2 retains a conformal shape after being molded. In another exemplary embodiment, the packing density and fabric material may be chosen to produce a generally conformal pillow. In yet another exemplary embodiment, the fabric material, filler material and packing density may be chosen to provide a more resilient characteristic.

When "frozen" i.e., stored at a low temperature, filling material 30 and therefore the eye pillow retains a reduced temperature for an extended period of time to provide a soothing coolness while completely retaining its smooth deformability. For example, a plurality of small pellets of low density polyethylene may be cooled to a reduced temperature and remain at the reduced temperature for an extended period of time without retaining moisture or providing moisture to the surfaces of the eye pillow. Other thermal storage materials with smooth surfaces may be used in other exemplary embodiments. The freezing temperature does not compromise the surface smoothness of the beads or the deformability or moldability of the eye pillow. Alternatively stated, the eye pillow retains the same degree of deformability/moldability at a range of reduced temperatures below 32° F., as it has at room temperature. In one exemplary embodiment, ergoBeads® may be used as filler material 30. In other embodiments, the eye pillow may be filled with other soft and deformable material that slides easily over itself and retains its moldability after being stored at a low temperature for an extended time period.

Although the invention has been described in terms of an exemplary eye pillow, it is not intended to be limited thereto. In other exemplary embodiments, other therapeutic products that provide ergonomic comfort and/or orthopedic relief, may be formed using the aforementioned filler material packed inside a pouch formed of cotton Lycra or other comfortable material as described previously. The pouch may take on various shapes and be used to provide therapeutic relief to various portions of the user's anatomy. It may be worn, held, or variously positioned with respect to the user/wearer. The fabric and packing density may be chosen such that the therapeutic product is easily deformable or moldable at any temperature and in one embodiment the packing density may be chosen to enable the therapeutic product to retain its shape when molded. In another exemplary embodiment, the fabric material, filler material and packing density may be chosen to provide a more resilient characteristic. The therapeutic products may include but are not limited to a squeezable stress ball for isometric hand exercise and strengthening, a pillow to rest one's head upon, a back pillow and variously configured wrist supports upon which to rest a user's wrist when operating a keyboard, mouse or other similar equipment, for example a wrist rest for laptop users. In other exemplary embodiments, the therapeutic product may be a product designed to be worn by the user such as a glove, a knee or elbow support, or other similar products.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical,", "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the device be constructed or operated in a particular orientation.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. An eye pillow comprising a duality of fabric panels joined together to form a closed pouch, the fabric panels forming opposed sides of said eye pillow and filled with a plurality of beads therebetween with no barrier between said plurality of beads and said fabric panels, each of said opposed sides conformable to a user's eye socket anatomy and including a duality of recessed portions, each corresponding to one of said user's eyes when said eye pillow is positioned on said user, each said recessed portion completely surrounded by a non-recessed portion.

2. The eye pillow as in claim 1, wherein each said recessed portion provides clearance for said user's eye and eyelashes when peripheral portions of said user's eye socket contact a facing one of said fabric panels.

3. The eye pillow as in claim 1, wherein said fabric panels are resiliently stretchable.

4. The eye pillow as in claim 1, wherein each of said fabric panels is a single and continuous section of textile and said fabric panels are joined peripherally.

5. The eye pillow as in claim 4, wherein each said recessed portion is formed at a non-peripheral location where said panels are joined conterminously together.

6. The eye pillow as in claim 5, wherein said fabric panels are joined together by stitching.

7. The eye pillow as in claim 1, wherein said beads are composed of low density polyethylene (LDPE).

8. The eye pillow as in claim 1, wherein said beads are oval or elliptical in shape, include a dimple and have no length greater than about 4.5 mm.

9. The eye pillow as in claim 1, wherein said beads include an average surface roughness of less than 100 nm.

10. The eye pillow as in claim 1, wherein said beads are formed of a thermal storage material capable of retaining a reduced temperature.

11. The eye pillow as in claim 10, wherein said reduced temperature is below 32° F., and said beads include an average surface roughness of less than 100 nm at said reduced temperature.

12. The eye pillow as in claim 1, wherein said eye pillow includes a generally level top portion and a duality of downwardly extending lobes.

13. The eye pillow as in claim 1, wherein said beads are packed together tightly enough such that said eye pillow is capable of retaining a conformal shape when molded.

14. The eye pillow as in claim 1, wherein said eye pillow has a first deformability at room temperature and retains said first deformabilty at a range of reduced temperatures below 32° F.

15. The eye pillow as in claim 1, further comprising a securing member coupled to said fabric panels to secure said eye pillow to said user's head.

16. The eye pillow as in claim 1, further comprising a lubricating medium at least one of coating said beads and disposed among said plurality of beads.

17. The eye pillow as in claim 16, wherein said lubricating medium comprises a powdery substance formed of an amide material.

18. The eye pillow as in claim 1, wherein said fabric panels are flaccid.

19. An eye pillow comprising a duality of textile panels joined together to form opposed sides of said eye pillow and filled with a plurality of beads therebetween, each of said opposed sides conformable to a uSer's eye socket anatomy and including a duality of recessed portions, each corresponding to one of said users eyes when said eye pillow is positioned on said user, wherein each said recessed portion is formed at a non-peripheral location where said panels are conterminously joined together, each said recessed portion completely surrounded by a non-recessed portion.

* * * * *

UNITED STATES PATENT AND TRADEMARK OFFICE
CERTIFICATE OF CORRECTION

| | | |
|---|---|---|
| PATENT NO. | : 7,601,168 B2 | Page 1 of 1 |
| APPLICATION NO. | : 11/141910 | |
| DATED | : October 13, 2009 | |
| INVENTOR(S) | : Aurelia Koby et al. | |

It is certified that error appears in the above-identified patent and that said Letters Patent is hereby corrected as shown below:

Column 4, line 8, replace "use's" with --user's--
    Claim 14, Column 8, line 9, replace "deformabilty" with --deformability--
    Claim 19, Column 8, line 25, replace "uSer's" with --user's--
    Claim 19, Column 8, line 27, replace "users" with --user's--

Signed and Sealed this

Sixteenth Day of February, 2010

David J. Kappos
*Director of the United States Patent and Trademark Office*

EX PARTE REEXAMINATION CERTIFICATE (12338th)

United States Patent
Koby et al.

(10) Number: US 7,601,168 C1
(45) Certificate Issued: Jul. 20, 2023

(54) EYE PILLOW

(75) Inventors: Aurelia Koby, San Diego, CA (US); Ian MacMorran, San Diego, CA (US)

(73) Assignee: BROWNMED, INC., Boston, MA (US)

Reexamination Request:
No. 90/014,612, Nov. 18, 2020

Reexamination Certificate for:
Patent No.: 7,601,168
Issued: Oct. 13, 2009
Appl. No.: 11/141,910
Filed: Jun. 1, 2005

Certificate of Correction issued Feb. 16, 2010

Related U.S. Application Data

(60) Provisional application No. 60/576,204, filed on Jun. 2, 2004.

(51) Int. Cl.
*A61F 7/00* (2006.01)
*A61F 7/02* (2006.01)

(52) U.S. Cl.
CPC ........ *A61F 7/02* (2013.01); *A61F 2007/0004* (2013.01); *A61F 2007/0204* (2013.01)

(58) Field of Classification Search
None
See application file for complete search history.

(56) References Cited

To view the complete listing of prior art documents cited during the proceeding for Reexamination Control Number 90/014,612, please refer to the USPTO's Patent Electronic System.

*Primary Examiner* — Patricia L Engle (57) ABSTRACT

A reversible eye pillow provides a set of opposed sides, each formed of a continuous fabric panel that is resiliently stretchable. Each side includes peripheral portions that conform to and contact peripheral portions of a user's eye and a recessed portion that enables a user to open his or her eye with the eye pillow in place. The eye pillow is tightly filled with small bead like thermal storage filling material that maintains a reduced temperature and includes a smooth surface to provide easy deformability of the eye pillow even at reduced temperatures.

US 7,601,168 C1

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE
SPECIFICATION AFFECTED BY AMENDMENT
ARE PRINT HEREIN.

Column 3, line 53-Column 4, line 17:
FIG. 3 is a partial cross sectional view of the eye pillow illustrating opposed surfaces 20, but the filler material that fills the eye pillow is not shown. Now referring to FIGS. 1 and 3, eye pillow 2 is shaped to conform to the anatomy of the user's face and each of downwardly extending lobes 6, separated by an indentation 22 to accommodate the user's nose, include peripheral portions 16 to contact the user's eye socket area, and recessed portions 12 corresponding to the position of the user's eyeballs. Recessed portions 12 may be formed by joining together opposed surfaces 20. The coupling of the opposed surfaces provides dimples or darts on each side. According to this exemplary embodiment, the thickness of eye pillow 2 is essentially the thickness of the two conterminously joined panels/surfaces at recessed portions 12 as there is no filling material therebetween. Dimpled or recessed portion 12 may laterally extend a distance that is at least the width of an eyeball. The opposed surfaces may be joined by stitching or other suitable means. When stitching is used, an "x" stitch *14* such as shown in FIG. 1, or other stitching configurations, may be used. In other exemplary embodiments, the opposed surfaces may be permanently or detachably joined using other suitable means. Depth 24 may vary and is advantageously chosen to provide clearance within which the user's eyeball and eyelashes may move when peripheral portions 16 contact the user's eye socket anatomy. As such, the wearer may open and move his or her eyes freely with the eye pillow maintaining undisturbed contact with surrounding portions such as the wearer's eyebrows, forehead, cheek, nose and other parts of the wearer's eye socket i.e., at peripheral portion 16, for added comfort. Maximum depth 26 between opposed surfaces 20 of eye pillow 2, may range from 0.25 inch to 2 or 3 inches according to one embodiment.

AS A RESULT OF REEXAMINATION, IT HAS BEEN DETERMINED THAT:

The patentability of claims 4-6, 8-9, 11 and 17 is confirmed.

Claims 1-3, 7, 10, 12-16 and 18-19 are cancelled.

New claims 20-29 are added and determined to be patentable.

*20. An eye pillow comprising a duality of fabric panels joined together to form a closed pouch, the fabric panels forming opposed sides of said eye pillow and filled with a plurality of beads therebetween with no barrier between said plurality of beads and said fabric panels, each of said opposed sides conformable to a user's eye socket anatomy and including a duality of recessed portions, each corresponding to one of said user's eyes when said eye pillow is positioned on said user, each said recessed portion completely surrounded by a non-recessed portion, wherein the recessed portions are free from openings that permit light to pass through, and further wherein the fabric panels are joined together to form the recessed portions.*

*21. An eye pillow comprising a duality of fabric panels joined together to form a closed pouch, the fabric panels forming opposed sides of said eye pillow and filled with a plurality of beads therebetween with no barrier between said plurality of beads and said fabric panels, each of said opposed sides conformable to a user's eye socket anatomy and including a duality of recessed portions, each corresponding to one of said user's eyes when said eye pillow is positioned on said user, each said recessed portion completely surrounded by a non-recessed portion, wherein the recessed portions block out light, and wherein the fabric panels are stitched together at the recessed portions.*

*22. An eye pillow comprising a duality of fabric panels joined together to form a closed pouch, the fabric panels forming opposed sides of said eye pillow and filled with a plurality of beads therebetween with no barrier between said plurality of beads and said fabric panels, each of said opposed sides conformable to a user's eye socket anatomy and including a duality of recessed portions, each corresponding to one of said user's eyes when said eye pillow is positioned on said user, each said recessed portion completely surrounded by a non-recessed portion, wherein each of the recessed portions is formed by "x" stitches.*

*23. An eye pillow comprising a duality of fabric panels joined together to form a closed pouch, the fabric panels forming opposed sides of said eye pillow and filled with a plurality of beads therebetween with no barrier between said plurality of beads and said fabric panels, each of said opposed sides conformable to a user's eye socket anatomy and including a duality of recessed portions, each corresponding to one of said user's eyes when said eye pillow is positioned on said user, each said recessed portion completely surrounded by a non-recessed portion, wherein the fabric panels are coupled together to form dimples at the recessed portions.*

*24. An eye pillow comprising a duality of fabric panels joined together to form a closed pouch, the fabric panels forming opposed sides of said eye pillow and filled with a plurality of beads therebetween with no barrier between said plurality of beads and said fabric panels, each of said opposed sides conformable to a user's eye socket anatomy and including a duality of recessed portions, each corresponding to one of said user's eyes when said eye pillow is positioned on said user, each said recessed portion completely surrounded by a non-recessed portion, the recessed portions block out light and wherein the fabric panels are conterminously joined together to form the recessed portions.*

*25. The eye pillow of claim 24, wherein a thickness of the eye pillow is equal to a thickness of the two fabric panels where the fabric panels are conterminously joined together.*

*26. An eye pillow comprising a duality of textile panels joined together to form opposed sides of said eye pillow and filled with a plurality of beads therebetween, each of said opposed sides conformable to a user's eye socket anatomy and including a duality of recessed portions, each corresponding to one of said user's eyes when said eye pillow is positioned on said user, wherein each said recessed portion is formed at a non-peripheral location where said panels are conterminously joined together, each said recessed portion completely surrounded by a non-recessed portion, wherein the recessed portions are free from openings that permit* light to pass through, and further wherein the textile panels are joined together to form the recessed portions.

27. An eye pillow comprising a duality of textile panels joined together to form opposed sides of said eye pillow and filled with a plurality of beads therebetween, each of said opposed sides conformable to a user's eye socket anatomy and including a duality of recessed portions, each corresponding to one of said user's eyes when said eye pillow is positioned on said user, wherein each said recessed portion is formed at a non-peripheral location where said panels are conterminously joined together, each said recessed portion completely surrounded by a non-recessed portion, wherein the recessed portions block out light, and wherein the textile panels are stitched together at the recessed portions.

28. An eye pillow comprising a duality of textile panels joined together to form opposed sides of said eye pillow and filled with a plurality of beads therebetween, each of said opposed sides conformable to a user's eye socket anatomy and including a duality of recessed portions, each corresponding to one of said user's eyes when said eye pillow is positioned on said user, wherein each said recessed portion is formed at a non-peripheral location where said panels are conterminously joined together, each said recessed portion completely surrounded by a non-recessed portion, wherein each of the recessed portions is formed by "x" stitches.

29. An eye pillow comprising a duality of textile panels joined together to form opposed sides of said eye pillow and filled with a plurality of beads therebetween, each of said opposed sides conformable to a user's eye socket anatomy and including a duality of recessed portions, each corresponding to one of said user's eyes when said eye pillow is positioned on said user, wherein each said recessed portion is formed at a non-peripheral location where said panels are conterminously joined together, each said recessed portion completely surrounded by a non-recessed portion, wherein the textile panels are coupled together to form dimples at the recessed portions.

* * * * *